(12) United States Patent
Lidgren et al.

(10) Patent No.: US 7,967,764 B2
(45) Date of Patent: Jun. 28, 2011

(54) DEVICE FOR MINI-INVASIVE ULTRASOUND TREATMENT OF AN OBJECT BY A HEAT-ISOLATED TRANSDUCER

(75) Inventors: Lars Lidgren, Lund (SE); Kaj Larsson, Lund (SE)

(73) Assignee: Ultrazonix DNT AB, Malmo (SE)

( * ) Notice: Subject to any disclaimer, the term of this patent is extended or adjusted under 35 U.S.C. 154(b) by 1012 days.

(21) Appl. No.: 10/500,814

(22) PCT Filed: Jan. 15, 2003

(86) PCT No.: PCT/SE03/00046
§ 371 (c)(1),
(2), (4) Date: Jul. 7, 2004

(87) PCT Pub. No.: WO03/059449
PCT Pub. Date: Jul. 24, 2003

(65) Prior Publication Data
US 2005/0054954 A1    Mar. 10, 2005

(30) Foreign Application Priority Data
Jan. 15, 2002  (SE) ...................................... 0200089

(51) Int. Cl.
*A61N 7/00*   (2006.01)
(52) U.S. Cl. ..................... 601/3; 601/2; 601/4; 600/439
(58) Field of Classification Search .......... 600/437–455; 601/1–4
See application file for complete search history.

(56) References Cited

U.S. PATENT DOCUMENTS

| 4,721,390 | A | * | 1/1988 | Lidgren .................. 366/139 |
| 4,787,371 | A | * | 11/1988 | Grasser et al. ................ 601/4 |
| 5,044,354 | A | * | 9/1991 | Goldhorn et al. ............. 601/4 |
| 5,285,772 | A | * | 2/1994 | Rattner ........................ 601/4 |
| 5,291,890 | A |   | 3/1994 | Cline et al. |
| 5,300,068 | A | * | 4/1994 | Rosar et al. ................. 606/34 |
| 5,327,890 | A | * | 7/1994 | Matura et al. .............. 600/427 |

(Continued)

FOREIGN PATENT DOCUMENTS
DE    3727692 C2    3/1989

(Continued)

OTHER PUBLICATIONS

European Search Report: EP09 16 0352.

*Primary Examiner* — Long V Le
*Assistant Examiner* — Sanjay Cattungal
(74) *Attorney, Agent, or Firm* — Ladas & Parry LLP

(57) ABSTRACT

The present invention relates to a device for mini-invasive ultrasound treatment of an object. At least one therapeutic ultrasound transducer (2) is arranged for treatment of the object (5) by generating an ultrasonic field (3), the temperature focus (F) of which is located in the object (5) for heating thereof. The therapeutic ultrasound transducer (2) comprises a probe (10) adapted to be inserted into the body in the direction towards the object (5) and comprises a front portion (10a) adapted to be located at, against or in the object (5). Said probe (10) comprises at least one transmitter element (11) for generating said ultrasonic field (3). The transmitter element (11) for generating the ultrasonic field (3) is arranged behind the front portion (10a) such that the transmitter element (11) does not heat or substantially not heat the front portion (10a) when in operation.

26 Claims, 3 Drawing Sheets

U.S. PATENT DOCUMENTS

Figure 1:
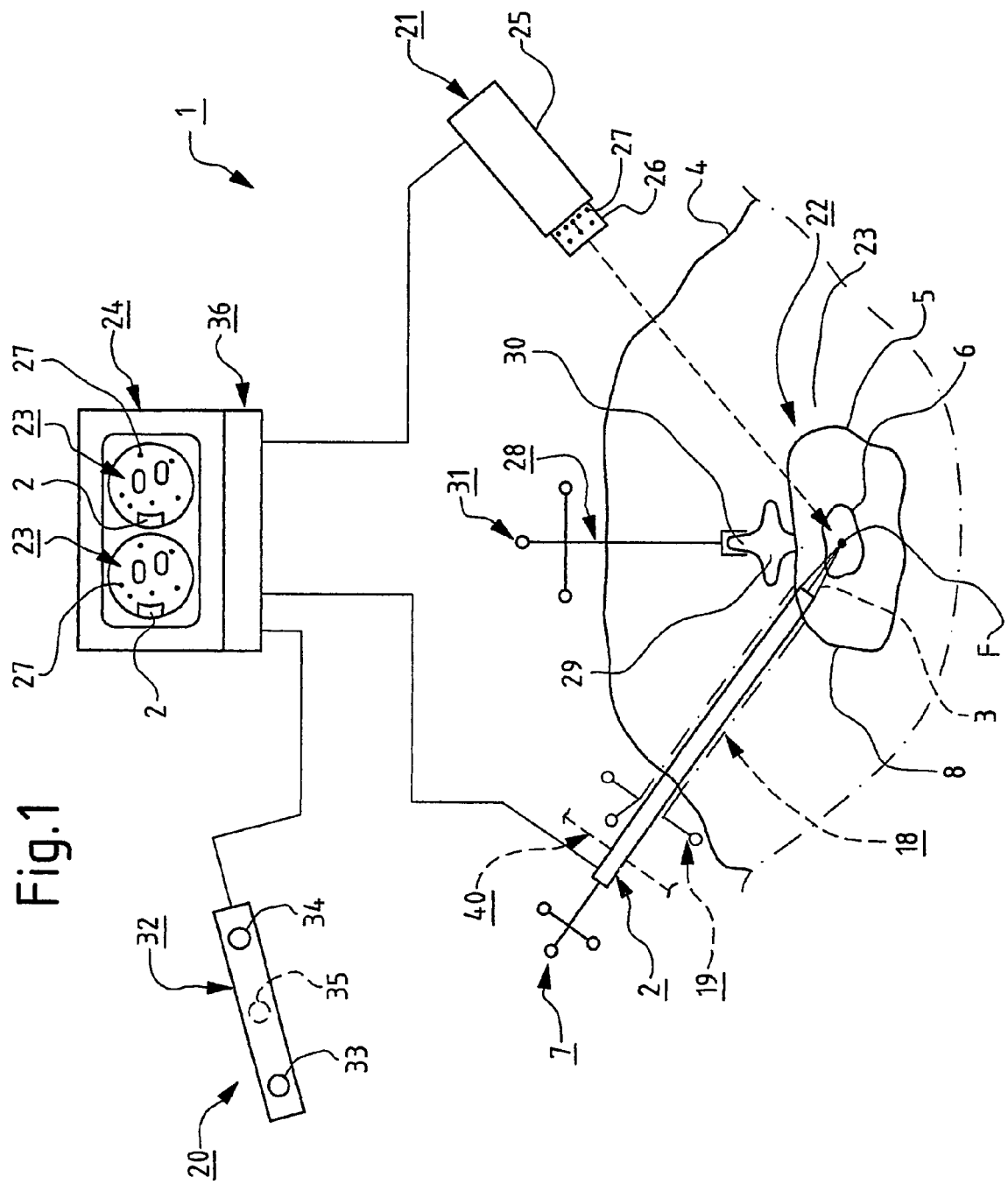

| | | | |
|---|---|---|---|
| 5,383,454 A | 1/1995 | Bucholz | |
| 5,471,988 A | 12/1995 | Fujio et al. | |
| 5,501,655 A | 3/1996 | Kolt et al. | |
| 5,620,479 A | 4/1997 | Diederich | |
| 5,720,287 A | 2/1998 | Chapelon et al. | |
| 5,733,315 A | 3/1998 | Burdette et al. | |
| 5,772,594 A | 6/1998 | Barrick | |
| 5,785,705 A | 7/1998 | Baker | |
| 5,834,759 A | 11/1998 | Glossop | |
| 5,980,504 A | 11/1999 | Sharkey et al. | |
| 6,007,570 A | 12/1999 | Sharkey et al. | |
| 6,021,343 A | 2/2000 | Foley et al. | |
| 6,073,051 A | 6/2000 | Sharkey et al. | |
| 6,267,734 B1* | 7/2001 | Ishibashi et al. | 601/2 |
| 6,379,320 B1* | 4/2002 | Lafon et al. | 601/3 |
| 6,599,288 B2* | 7/2003 | Maguire et al. | 606/27 |
| 6,821,274 B2* | 11/2004 | McHale et al. | 606/41 |
| 6,971,994 B1* | 12/2005 | Young et al. | 601/3 |
| 2001/0007940 A1 | 7/2001 | Tu et al. | |
| 2002/0193784 A1* | 12/2002 | McHale et al. | 606/27 |
| 2003/0130657 A1* | 7/2003 | Tom et al. | 606/47 |
| 2005/0020918 A1* | 1/2005 | Wilk et al. | 600/439 |
| 2005/0043726 A1* | 2/2005 | McHale et al. | 606/27 |
| 2005/0271996 A1* | 12/2005 | Sporbert et al. | 433/24 |
| 2006/0235300 A1* | 10/2006 | Weng et al. | 600/439 |

FOREIGN PATENT DOCUMENTS

| | | |
|---|---|---|
| DE | 4311327 C2 | 10/1994 |
| EP | 0668052 | 1/2003 |
| EP | 0 782 125 B1 | 7/2003 |
| FR | 2715822 A1 | 8/1995 |
| HU | 219085 B | 10/1995 |
| JP | 1-0248850 A | 9/1998 |
| RU | 99124888 | 8/2001 |
| WO | 97/35518 A1 | 10/1997 |
| WO | WO0023147 | 4/2000 |
| WO | WO0205897 | 1/2002 |

* cited by examiner

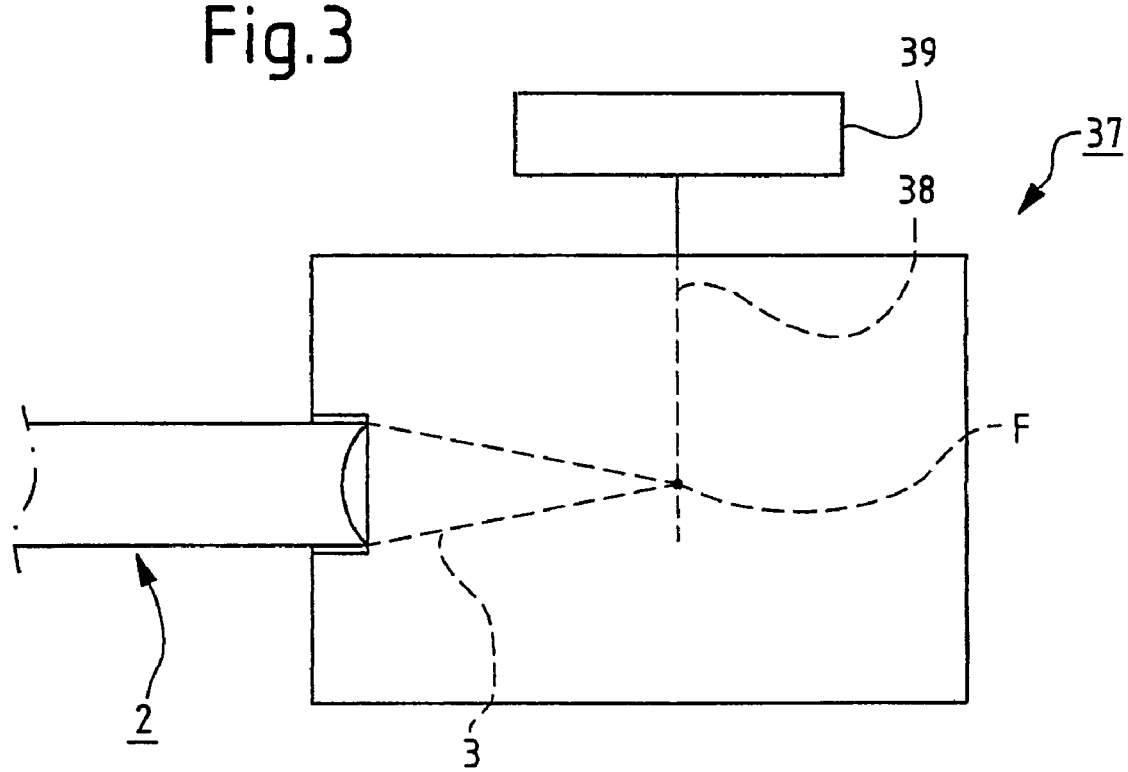

DEVICE FOR MINI-INVASIVE ULTRASOUND TREATMENT OF AN OBJECT BY A HEAT-ISOLATED TRANSDUCER

The present invention relates to a device for mini-invasive ultrasound treatment of an object of a patient, wherein at least one therapeutic ultrasound transducer is arranged for treatment of the object by generating an ultrasonic field having a temperature focus located in the object for heating thereof, wherein the therapeutic ultrasound transducer comprises a probe adapted to be inserted into the body in the direction towards the object to be treated, and comprises a front portion adapted to be placed at, against or in the object and whereby said probe comprises at least one transmitter element for generating said ultrasonic field, which transmitter element is allowed to be heated in operation.

The intervertebral disc consists of an outer fibrous tissue ring, annulus fibrosus, and an inner, more viscous part, nucleus pulposus. The disc functions as a shock absorber and if annulus fibrosus breaks, e.g. by a small fissuring, disc matter may find its way out and cause a compression of nerve roots and induce an inflammatory reaction.

Prolapsed intervertebral discs have been treated surgically since the thirties by removal of the displaced disc matter and/or a part of the bulging disc. Later, the surgical treatment has developed towards less invasive operations and now, percutaneous techniques are used for removing disc matter. An alternative method for surgical treatment is chemonucleolysis, where the enzyme chymopapain is injected into nucleus pulposus, the central part of the disc. The enzyme polymerizes the long proteoglycan chains in nucleus pulposus with subsequent loss of the hygroscopicity. This reduces the volume and pressure in nucleus pulposus and the bulging part of the disc, which explains the pain relief patients with sciatica experience after chemonucleolysis. The method has proven to give pain relief in 75 percent of the cases and has a well documented cost efficiency. Unfortunately, the method has caused serious allergic reactions in about 1 percent of the cases. Next step in the development could be a non-invasive treatment of prolapsed inter-vertebral discs, which preferably should be painless, avoid the risk for infections and carried through ambulatory.

A method for thermotherapy and coagulation of tissue involves use of focused ultrasound with high intensity. The ultrasound passes well through soft tissue and can be focused on remote spots within a surface of a few millimeters. The energy absorption in the tissue increases the temperature with a sharp temperature gradient such that the boundaries of the treated volume are clearly limited without causing any damages on the surrounding tissue (U.S. Pat. No. 5,291,890, U.S. Pat. No. 5,501,655). Ultrasound treatment of prolapsed intervertebral discs is previously known (EP 0 872 262).

Heat treatment of discs has proven successful in a method called IDET (U.S. Pat. No. 6,073,051, U.S. Pat. No. 6,007,570, U.S. Pat. No. 5,980,504). The method has as its aim to insert a catheter into the disc by means of a cannula. Farthest out on the catheter there is a coil which is heated by applying a radio frequency voltage thereon (U.S. Pat. No. 5,785,705). The heat is increased to about 90° C. in nucleus pulposus where the heating element of the catheter has been located and treatment is carried through for 15 minutes.

Surgery with focused ultrasound has several advantages compared with other thermal techniques. The focus can be made movable and the energy can be supplied during short time intervals. The limitation of ultrasound is its absorption in bone and its poor penetration through gasfilled passages. Clinical applications of ultrasound surgery are today mostly used in ophthalmic surgery, urology and oncology. The effect of ultrasound can be divided into thermal and non-thermal effects.

The thermal effects of ultrasound are caused by absorption of ultrasound in the tissue. This leads to a temperature increase which is dependent on the parameters of the ultrasound (frequency and intensity) and the acoustic properties of the tissue. The absorption of ultrasound in musculoskeletal tissues increases with the apatite and protein content, which means high absorption in bone, cartilage, tendons and ligaments. Water however, has a low ultrasound absorption capacity and can for this reason be used as an acoustic medium between the ultrasound transducer and the tissue. Higher absorption can be expected in annulus fibrosus (high collagen content) than in nucleus pulposus (high water concentration). This will lead to higher temperatures in the outer part of the intervertebral disc than in the central part. In order to avoid that the temperature in annulus fibrosus exceeds a detrimental level at the same time as the temperature in nucleus pulposus reaches a sufficient level, the ultrasound can be transmitted from several ultrasound sources. In this manner, the fields will overlap each other and increase the effect in nucleus pulposus at the same time as the intensity in the surrounding tissue including annulus fibrosus can be kept low.

In mini-invasive ultrasound treatment, the therapeutic ultrasound transducer is inserted through a small cut in the skin of the patient and moved towards the object to be treated. Since the ultrasound transducer is heated during operation, a risk exists that the tissue close to the treatment area is exposed to unacceptable high heat influence.

The object of the present invention is to overcome the above-mentioned heat problem. This is achieved according to the invention by means of a device mainly having the characterizing features of subsequent claim 1.

By means of a transmitter element arranged in a rear portion behind a front portion of the probe, which front portion is to be located at, against or in the object to be treated, it is achieved that the transmitter element does not heat or substantially not heat said front portion, i.e. one achieves a thermal insulation between the transmitter element, which is heated during ultrasound generation, and the tissue at which the front portions of the probe are located during the treatment.

Figure 2:
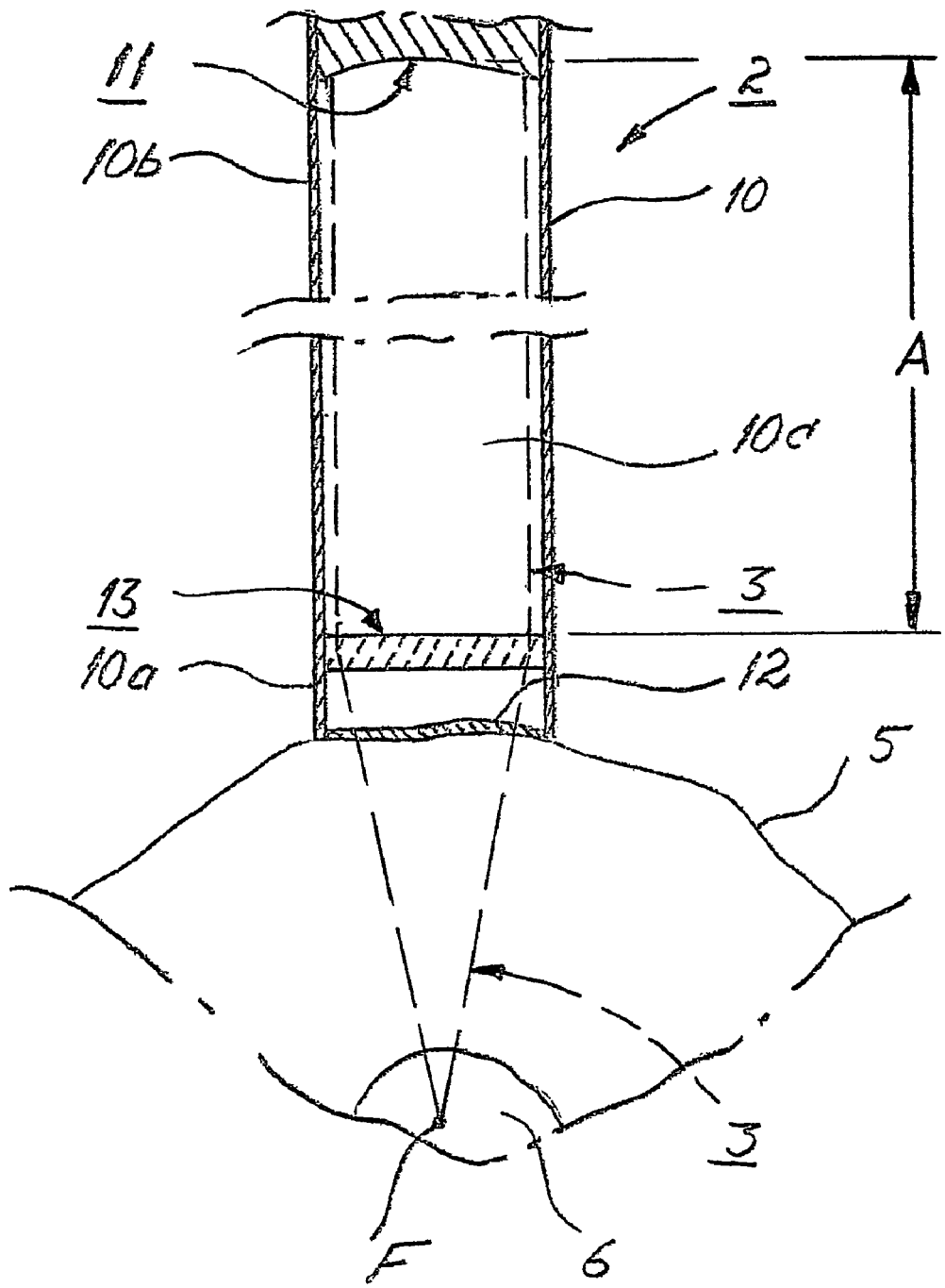

The invention will be further described below with reference to the accompanying drawings, in which FIG. 1 schematically shows a constructive embodiment of the device according to the invention;

FIG. 2 schematically shows parts of a therapeutic ultrasound transducer comprised in a device according to FIG. 1; and FIG. 3 schematically shows a calibrating device which can be comprised in a device according to FIG. 1.

The treatment device 1 schematically illustrated in FIG. 1 is intended for producing, by means of at least one therapeutic ultrasound transducer 2 (so called therapeutic transducer), an ultrasonic field 3, the temperature focus F of which is intended to be located in an object 5 of the patient 4 for treatment thereof. The object can for example be the nucleus pulposus 6 in an intervertebral disc 5 of the patient 4, but it can also be another object such as a ligament in e.g. a shoulder, knee, elbow or a foot. However, in the description text below reference will be made to the treatment of a disc.

The therapeutic ultrasound transducer 2 is in this example intended to be inserted through the patient's 4 skin, e.g. by means of a cut or by means of a cannula, and contact the disc 5, preferably annulus fibrosus 8, to achieve a local temperature increase in nucleus pulposus 6 so that enzymes such as collagenase present in the disc are activated and cause decomposition of collagen and proteoglycanes, which results in shrinking of nucleus pulposus 6 primarily because of less hygroscopicity. A heating to for example 60-70 degrees Celsius can directly achieve a destruction—a change in the structure of proteoglycane. The therapeutic ultrasound transducer 2 can be placed against the disc 5 without perforating the annulus fibrosus 8 and from there transmit the ultrasonic field 3 focused in the temperature focus F towards the treatment volume.

The therapeutic ultrasound transducer 2 comprises a probe 10, which preferably is an elongated probe 10. The front portion or portions 10a of the probe 10 can be positioned in contact with the disc 5. At least one transmitter element 11, e.g. a piezoelectric element, is arranged in such a portion 10b, herein called a rear portion 10b, of the probe 10 which is located behind said front portion 10a such that the transmitter element 11 heated during operation does not heat or substantially not heat the front portion 10a of the probe 10 or the tissue surrounding said front portion 10a.

According to an embodiment of the invention, the electronics is located in or attached to such part of the probe, i.e. in the rear portion of the probe, which is arranged on the outside of the patient during treatment. Thus no or a reduced amount of electronics is located inside the patient during treatment.

The front portion 10a of the probe 10 is preferably configured to be thermally insulating. For example, the front portion 10a can be manufactured of or comprise Pyrex™ or another suitable material.

The front portion 10a of the probe 10 can be closed in the front part, e.g. by means of a flexible wall 12 of suitable material. Further, the front portion 10a of the probe 10 can comprise or be attached to a focussing device 13 in order to focus the ultrasound field 3 generated by the transmitter element 11. Said focussing device 13 can for example be arranged adjacent the flexible wall 12.

The distance A between the transmitter element 11 and the focussing device 13 can be in the range of 0.5-20 centimeters and preferably in the range of 1-18 centimeters.

A space 10c in the probe 10 between the transmitter element 11 and the focussing device 13 can be arranged to and/or comprise such material that only small power losses of the ultrasonic field 3 arise therein.

If said space 10c comprises material, the material can be adapted to exert a focusing effect on the ultrasonic field 3 either alone or together with the focussing device 13.

The treatment device 1 can comprise a rigid tube 18 with associated inner portion and several position transmitters 19, preferably at least three such transmitters. The tube 18 can, by means of optical navigation technique, be inserted towards the object 5 to be treated. It can for example be inserted dorsolaterally towards the disc 5. The inner portion of the tube 18 is then replaced by the therapeutic ultrasound transducer 2 and said tube 18 is schematically illustrated in FIG. 1 with broken lines.

The treatment device 1 can also comprise an optical navigating device 20 for navigation of the therapeutic ultrasound transducer 2 (U.S. Pat. No. 5,772,594). This optical navigating device 20 comprises at least one diagnostic camera 21 which is adapted to produce at least one image of the anatomical structure 23 of the treatment area 22 in a monitor 24. The diagnostic camera 21 can be an X-ray camera 25 taking two pictures of the anatomical structure 23 of the treatment area 22 from different directions with preferably a 90° intermediate angle and displaying these pictures in the monitor 24. At the optical navigating device 20, the X-ray camera 25 is used together with an optical analog-digital-converter for obtaining a real time image in the monitor 24 of the position and direction of the therapeutic ultrasound transducer 2 (U.S. Pat. No. 6,021,343, U.S. Pat. No. 5,834,759, U.S. Pat. No. 5,383,454).

The X-ray camera 25 comprises a positioning device 26—e.g. a cylindrical cover—which is located in front of the object of the X-ray camera 25 and having markers 27 the mutual distances of which are known. The markers 27 can be round and consist of a metallic material e.g. tantalum.

In the optical navigating device 20, a reference device 28 can further be comprised. In the case of treatment of a disc, the reference device 28 is arranged to be attached to the spinous process 30 of a vertebra 29 or in a corresponding position such that it gets a determined position relative to the treatment area 22. The reference device 28 can comprise several position transmitters 31, preferably at least three, and these can consist of metallic material, e.g. tantalum.

The therapeutic ultrasound transducer 2 can comprise a plurality, preferably three or more, position transmitters 7 to determine its position.

Furthermore, the optical navigating device 20 can comprise a signal receiving and/or signal sending unit 32. This unit can comprise a suitable number of signal receivers 33, 34 for receiving signals from the position transmitters 7 and 31 of the therapeutic ultrasound transducer 2 and the reference device 28, respectively. The signal receiving and/or signal sending unit 32 can possibly comprise one or more signal transmitters 35 for transmitting signals to said position transmitters 7 and 31, which are arranged to receive these signals.

The signals transmitted by the position transmitters 7 and 31 can e.g. be in the form of infrared light or visible light or radio frequency electromagnetic waves or acoustic waves and the signal receivers 33, 34 can in such case be receivers of infrared light or visible light or radio frequency electromagnetic waves or acoustic waves.

In the treatment device 1 there can also be included a calibrating unit 37 for calibrating the temperature effect of the temperature focus F of the therapeutic ultrasound transducer 2. The calibrating unit 37 has one or more thermoelements 38 by means of which the effect at said temperature focus F can be measured for calibration. The thermoelements 38 are connected to a schematically illustrated measuring device 39.

The calibrating unit 37 can be arranged to measure the output power by means of the echo of an ultrasound transducer, which ultrasound transducer can be a separate one. The calibrating unit 37 can further be arranged to measure the echo from the therapeutic ultrasound transducer 2.

Prior to treatment of the disc 5, preferably nucleus pulposus 6, the reference device 28 can be located on the patient's 4 vertebra 29 and the therapeutic ultrasound transducer 2 is calibrated in the calibrating unit 37.

Two X-ray images can be taken of the patient's 4 anatomical structure 23 at the disc 5 and these X-ray images are displayed on the monitor 24. On these X-ray images, the position of the reference device 28 relative to the disc 5 can then be determined by means of the markers 27 of the positioning device 26.

During treatment of the disc 5, preferably nucleus pulposus 6, the therapeutic ultrasound transducer 2 can be navigated by means of the signal receiving or signal sending unit 32, whereby the navigation is presented in the X-ray images on the monitor 24. This is accomplished in that the position transmitters 7 of the therapeutic ultrasound transducer 2 cooperating through signals with the signal transmitters 33, 34 of the signal receiving or signal sending unit 32. By means of said navigation, the therapeutic ultrasound transducer 2 can be positioned such that the temperature focus F of its ultrasonic field 3 will fall in the disc 5, preferably nucleus pulposus 6. The temperature in the temperature focus F preferably exceeds 45° C.

The treatment can be automatically interrupted if the patient 4 moves to an incorrect position relative to the therapeutic ultrasound transducer 2 or vice versa.

The invention is not limited to the method described above, but can vary within the scope of the following claims. Thus, the object 5 can be another object in the body than a disc that is to be treated and the disc can be any disc in the body.

The diagnostic camera 21 can be a computerized tomography (CT) scanner which is arranged to produce images of said anatomical structure 23 and these images can be processed in a computer program or software for obtaining a 3D-image in the monitor 24. The diagnostic camera 21 can alternatively be an X-ray camera or a magnetic resonance imaging (MRI) camera, which is arranged to generate images of said anatomical structure 23 and these images can be processed in a computer program for obtaining a 3D-image in the monitor 24.

The therapeutic ultrasound transducer 2 can be arranged to be positioned manually or be arranged at a positioning device 40 for positioning the same relative to the disc 5 to be treated.

The probe 10 can be provided with a cooling device (not shown) comprising channels conducting cooling liquid around the tip of the probe 10, which tip can be provided with a membrane. However, according to another embodiment of the invention, the tip of the probe is not provided with a membrane. In such an embodiment the tip of the probe can be located adjacent to the object to be treated and the cooling liquid can be conducted around the tip in the space between the tip and the object to be treated.

The described apparatus can be used in methods for treatment of discs but also for treatment of other objects in the body. As examples of such other objects can be mentioned ligament in for example shoulders, knees, elbows or feet.

Further, it should be understood that dependent on the object to be treated different steps and components described above can be excluded. The optical navigation device and/or the reference device can for example be excluded in the case of treatment of a ligament in e.g. knee since this structure has a site more easy to determine than for example an intervertebral disc.

The invention claimed is:

1. A device for mini-invasive ultrasound treatment of an object comprising:
    at least one therapeutic ultrasound transducer arranged for treatment of the object by generating an ultrasonic field, the temperature focus of which is located in the object for heating thereof;
    the therapeutic ultrasound transducer comprising an elongated probe defining a longitudinal direction and being adapted to be introduced into a body towards the object to be treated and which elongated probe comprises a front portion adapted to be located at, against, or in the object; and wherein the elongated probe comprises at least one transmitter element for generating the ultrasonic field for treatment of the object and for transmitting the ultrasonic field through the front portion,
    wherein the transmitter element is arranged in a rear portion behind the front portion of the probe seen in the longitudinal direction, and wherein the front portion is configured to be thermally insulating, whereby during operation the transmitter element does not heat the front portion to a temperature sufficient to cause damage to the body,
    wherein the front portion of the probe comprises a focusing device for focusing the ultrasonic field generated by the transmitter element, and
    wherein the distance between the transmitter element and the focusing device for focusing the ultrasonic field in temperature focus is in the range of 0.5-20 centimeters.

2. Device according to claim 1, wherein the distance between the transmitter element and the focusing device for focusing the ultrasonic field in temperature focus is in the range of 1-18 centimeters.

3. Device according to claim 1, wherein the probe, in a space between the transmitter element and the focusing device for focusing the ultrasonic field in the temperature focus, is configured and/or comprises a material such that only small power losses in the ultrasonic field is obtained therein.

4. Device according to claim 1, wherein the probe, in a space between the transmitter element and the focusing device for focusing the ultrasonic field in the temperature focus, comprises a material adapted to exert a focusing effect on the ultrasonic field together with the focusing device.

5. Device according to claim 1, wherein an optical navigation device comprises at least one diagnostic camera arranged to generate at least one image of the anatomical structure of the treatment area within which the object to be treated is located.

6. Device according to claim 5, wherein the diagnostic camera is an X-ray camera.

7. Device according to claim 6, wherein the X-ray camera comprises a positioning device with markers which are intended to determine the position of the anatomical structure displayed in a monitor and present at the patient's disc to be treated.

8. Device according to claim 7, wherein the monitor is arranged to display two X-ray photographs of said anatomical structure taken with the X-ray camera from two different locations.

9. Device according to claim 5, wherein the diagnostic camera is a computerized tomography (CT) scanner which is arranged to produce images of the anatomical structure at the patient's object to be treated, which images being processed in a computer program (software) for obtaining a 3D-image in a monitor.

10. Device according to claim 5, wherein the diagnostic camera is an X-ray camera or a MRI scanner which is arranged to produce images of the anatomical structure at the patient's object to be treated, which images being processed in a computer program (software) for obtaining a 3D-image in a monitor.

11. Device according to claim 5, wherein the optical navigating device further comprises at least one signal receiving or signal sending unit which is intended to receive signals from and/or send signals to position transmitters on
    a) a reference device which has a set position relative to the object and
    b) the therapeutic ultrasound transducer such that the position thereof relative to said treatment area can be determined.

12. Device according to claim 11, wherein the signal receiving or signal sending unit is arranged to receive or send signals in the form of infrared light or visible light or radio frequency electromagnetic waves or acoustic waves and that said position transmitters are arranged to send or receive signals in the form of infrared light or visible light or radio frequency electromagnetic waves or acoustic waves.

13. Device according to claim 11 wherein the reference device is attached to a vertebra in the patient's vertebral column, preferably to the spinal process of said vertebra.

14. Device according to claim 11, wherein the reference device comprises position transmitters consisting of metallic balls, preferably tantalum balls.

15. Device according to claim 14, wherein the signal receiving or signal sending unit of the optical navigating device is at least one X-ray device.

16. Device according to claim 5, wherein a tube with an associated inner portion is insertable towards the object to be treated and that said inner portion is intended to be replaced by the therapeutic ultrasound transducer.

17. Device according to claim 16, wherein said tube is navigatable by means of the optical navigating device through the skin of the patient and brought into contact with the object to be treated.

18. Device according to claim 1, wherein the temperature in the temperature focus of the therapeutic ultrasound transducer exceeds 45° C.

19. Device according to claim 1, wherein a calibrating device is arranged for calibrating the power emitted by the therapeutic ultrasound transducer in the temperature focus of said therapeutic ultrasound transducer and/or the position of said temperature focus relative to the transmitter element of the therapeutic ultrasound transducer.

20. Device according to claim 19, wherein the calibrating device is arranged to measure the emitted power by means of the echo of an ultrasound transmitter.

21. Device according to claim 20, wherein the calibrating device is arranged to measure the echo from the therapeutic ultrasound transducer.

22. Device according to claim 1, wherein the probe is provided with a cooling device comprising channels conducting cooling liquid around the tip of the probe, which tip is provided with a membrane.

23. Device according to claim 1, wherein the device is arranged for mini-invasive ultrasound treatment of an object in the form of nucleus pulposus in the patient's disc.

24. Device according to claim 23, wherein the therapeutic ultrasound transducer is arranged to be inserted through the patient's skin through a cut therein or by means of a cannula and brought into contact with the disc which annulus fibrosus is to be treated.

25. Device according to claim 1, wherein the device is arranged for mini-invasive ultrasound treatment of objects in the form of ligaments in shoulders of knees.

26. Device according to claim 1, wherein electronics are located in or attached to the rear portion of the probe and arranged on the outside of the patient during treatment.

* * * * *